United States Patent
Kim et al.

(10) Patent No.: US 11,097,996 B2
(45) Date of Patent: Aug. 24, 2021

(54) METHOD FOR SEPARATING ETHYLENE OLIGOMERIZATION REACTION PRODUCTS

(71) Applicant: LG Chem, Ltd., Seoul (KR)

(72) Inventors: Mi Kyung Kim, Daejeon (KR); Eun Kyo Kim, Daejeon (KR); Jeong Seok Lee, Daejeon (KR)

(73) Assignee: LG Chem, Ltd.

( * ) Notice: Subject to any disclaimer, the term of this patent is extended or adjusted under 35 U.S.C. 154(b) by 0 days.

(21) Appl. No.: 15/734,858

(22) PCT Filed: Nov. 15, 2019

(86) PCT No.: PCT/KR2019/015674
§ 371 (c)(1),
(2) Date: Dec. 3, 2020

(87) PCT Pub. No.: WO2020/122441
PCT Pub. Date: Jun. 18, 2020

(65) Prior Publication Data
US 2021/0230085 A1    Jul. 29, 2021

(30) Foreign Application Priority Data
Dec. 10, 2018  (KR) .................. 10-2018-0158229

(51) Int. Cl.
*C07C 11/107* (2006.01)
*C07C 2/08* (2006.01)
(Continued)

(52) U.S. Cl.
CPC .............. *C07C 11/107* (2013.01); *C07C 2/08* (2013.01); *C07C 7/04* (2013.01); *C08F 4/69* (2013.01); *C08F 2/06* (2013.01); *C08F 10/02* (2013.01)

(58) Field of Classification Search
CPC . C07C 11/107; C07C 2/08; C07C 7/04; C08F 4/69; C08F 2/06; C08F 10/02
See application file for complete search history.

(56) References Cited

U.S. PATENT DOCUMENTS

| 5,521,264 A | 5/1996 | Mehra et al. |
| 5,681,908 A | 10/1997 | Mehra et al. |

(Continued)

FOREIGN PATENT DOCUMENTS

| KR | 19980702777 A | 8/1998 |
| KR | 20090086907 A | 8/2009 |

(Continued)

OTHER PUBLICATIONS

International Search Report for Application No. PCT/KR2019/015674, dated Feb. 25, 2020, pp. 1-2.

*Primary Examiner* — Ali Z Fadhel
(74) *Attorney, Agent, or Firm* — Lerner, David, Littenberg, Krumholz & Mentlik, LLP (57) ABSTRACT

A method for separating ethylene oligomerization reaction products is provided. The method improves energy efficiency by controlling the temperature of the ethylene oligomerization reaction products. When the method for separating the ethylene oligomerization reaction products of the present invention is used, it is possible to minimize the use of hot utility and save costs required for a separation process.

11 Claims, 1 Drawing Sheet

(51) Int. Cl.
*C08F 4/69* (2006.01)
*C07C 7/04* (2006.01)
*C08F 2/06* (2006.01)
*C08F 10/02* (2006.01)

(56) References Cited

U.S. PATENT DOCUMENTS

| | | | |
|---|---|---|---|
| 2009/0203951 A1* | 8/2009 | Kurukchi | ................. B01D 3/14 585/648 |
| 2014/0012059 A1* | 1/2014 | Vinel | ....................... C07C 7/04 585/809 |
| 2015/0299069 A1 | 10/2015 | Azam et al. | |
| 2018/0044266 A1 | 2/2018 | Jeong et al. | |
| 2018/0319949 A1 | 11/2018 | Lee et al. | |

FOREIGN PATENT DOCUMENTS

| | | | |
|---|---|---|---|
| KR | 20150088249 A | 7/2015 | |
| KR | 20160144805 A | 12/2016 | |
| KR | 20170074658 A | 6/2017 | |
| KR | 20170141872 A | 12/2017 | |
| WO | WO-2009136985 A2 * | 11/2009 | ............. B01D 3/146 |

* cited by examiner

METHOD FOR SEPARATING ETHYLENE OLIGOMERIZATION REACTION PRODUCTS

CROSS-REFERENCE TO RELATED APPLICATIONS

The present application is a national stage entry under 35 U.S.C. § 371 of International Application No. PCT/KR2019/015674 filed on Nov. 15, 2019, which claims priority to Korean Patent Application No. 2018-0158229, filed on Dec. 10, 2018, in the Korean Intellectual Property Office, the disclosures of which are incorporated herein in their entirety by reference.

TECHNICAL FIELD

The present invention relates to a method for separating ethylene oligomerization reaction products, the method improving energy efficiency by controlling the temperature of the ethylene oligomerization reaction products.

BACKGROUND ART

A linear alpha-olefin is commercially widely used as an important material in a co-monomer, a cleaner, a lubricant, a plasticizer, and the like. Specifically, 1-hexene and 1-octene are used as a co-monomer for controlling the density of polyethylene when preparing a linear low density polyethylene (LLDPE).

Such a linear alpha-olefin is typically prepared through an oligomerization reaction of ethylene. The ethylene oligomerization reaction is performed by an oligomerization reaction of ethylene (trimerization reaction or tetramerization reaction) by using the ethylene as a reactant. Reaction products produced by a polymerization reaction of the ethylene are composed of unreacted ethylene, a solvent needed to dissolve a catalyst and the ethylene during the polymerization reaction, linear alpha-olefins of various carbon numbers polymerized by the reaction, and the like, and are separated into desired products by passing through a plurality of distillation columns. Specifically, the reaction product flow passes through a distillation column separating unreacted ethylene, and a separation purification process is performed for product and solvent recovery. Distillation using a boiling point difference is typically used, and when using a distillation column, heat supply and heat removal are required, and in order to solve the problem, hot utility, cooling water, and the like are excessively used, thereby increasing operation costs.

Therefore, studies for finding out a method capable of efficiently separating reactants produced by the ethylene polymerization reaction with low energy alone and reducing production costs and energy usage are being performed.

PRIOR ART DOCUMENT

Patent Document (Patent Document 1) KR 2015-0088249 A

DISCLOSURE OF THE INVENTION
TECHNICAL PROBLEM

An aspect of the present invention provides a method for separating ethylene oligomerization reaction products, the method improving energy efficiency by using at least a portion of an oligomer fraction produced by an ethylene oligomerization reaction as a heat source for a reboiler of a solvent distillation column.

Another aspect of the present invention provides a method for separating ethylene oligomerization reaction products, the method improving energy efficiency by using at least a portion of a third upper fraction discharged from the top of a solvent distillation column as a heat source for a reboiler of each of a first C6 distillation column and a second C6 distillation column.

Technical Solution

According to an aspect of the present invention, there is provided a method for separating ethylene oligomerization reaction products, the method including introducing an oligomer fraction excluding unreacted ethylene and 1-butene among ethylene oligomerization reaction products into a cooling unit to be cooled, introducing the oligomer fraction discharged from the cooling unit into a first C6 distillation column to discharge a first upper fraction from the top of the first C6 distillation column and discharge a first lower fraction from the bottom of the first C6 distillation column, introducing the first upper fraction discharged from the top of the first C6 distillation column into a second C6 distillation column to discharge a second upper fraction from the top of the second C6 distillation column and discharge a second lower fraction from the bottom of the second C6 distillation column, and introducing the first lower fraction discharged from the bottom of the first C6 distillation column into a solvent distillation column to discharge a third upper fraction from the top of the solvent distillation column and discharge a third lower fraction from the bottom of the solvent distillation column, wherein the first C6 distillation column, the second C6 distillation column, and the solvent distillation column are each provided with a condenser and a reboiler, at least a portion of the oligomer fraction is used as a reboiler heat source for the solvent distillation column, and at least a portion of the third upper fraction is used as a reboiler heat source for each of first C6 distillation column and the second C6 distillation column.

Advantageous Effects

When a method for separating ethylene oligomerization reaction products of the present invention is performed, at least some of high-temperature ethylene oligomerization reaction products are used as a heat source for a reboiler of a different distillation column, for example, a solvent distillation column, and a high-temperature flow discharged from the solvent distillation column, for example, at least a portion of a third upper fraction discharged from the top of the solvent distillation column is used as a heat source for a reboiler of each of a first C6 distillation column and a second C6 distillation column, so that the use of hot utility is minimized to increase energy efficiency and costs required for a separation process are saved.

MODE FOR CARRYING OUT THE INVENTION

Figure 1:
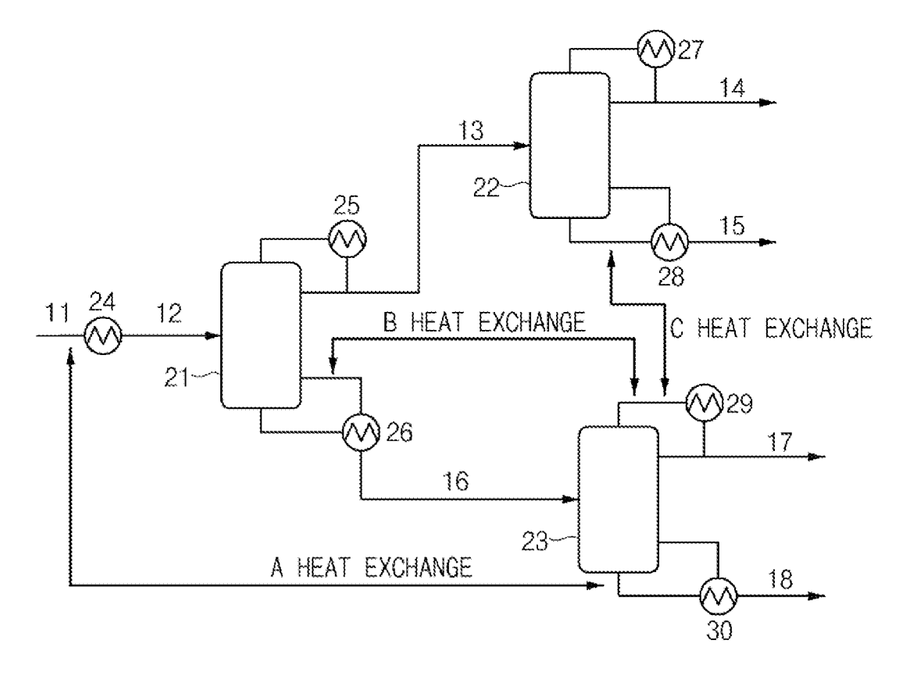
The FIGURE is a process diagram for illustrating a method for separating ethylene oligomerization reaction products according to an embodiment of the present invention.

Hereinafter, the present invention will be described in more detail to facilitate understanding of the present invention.

It will be understood that words or terms used in the description and claims of the present invention shall not be construed as being limited to having the meaning defined in commonly used dictionaries. It will be further understood that the words or terms should be interpreted as having meanings that are consistent with their meanings in the context of the relevant art and the technical idea of the invention, based on the principle that an inventor may properly define the meaning of the words or terms to best explain the invention.

According to an aspect of the present invention, there is provided a method for separating ethylene oligomerization reaction products, the method characterized by including introducing an oligomer fraction from which unreacted ethylene and 1-butene is remove among ethylene oligomerization reaction products into a cooling unit to be cooled, introducing the oligomer fraction discharged from the cooling unit into a first C6 distillation column to discharge a first upper fraction from the top of the column and discharge a first lower fraction from the bottom of the column, introducing the first upper fraction discharged from the top of the first C6 distillation column into a second C6 distillation column to discharge a second upper fraction from the top of the column and discharge a second lower fraction from the bottom of the column, and introducing the first lower fraction discharged from the bottom of the first C6 distillation column into a solvent distillation column to discharge a third upper fraction from the top of the column and discharge a third lower fraction from the bottom of the column, wherein the first C6 distillation column, the second C6 distillation column, and the solvent distillation column are each provided with a condenser and a reboiler, at least a portion of the oligomer fraction is used as a reboiler heat source for the solvent distillation column, and at least a portion of the third upper fraction is used as a reboiler heat source for each of first C6 distillation column and the second C6 distillation column.

Hereinafter, the present invention will be described in detail with reference to the accompanying drawings.

The FIGURE is a process diagram for illustrating a method for separating ethylene oligomerization reaction products according to an embodiment of the present invention.

In the present invention, an 'oligomer' means a low polymer formed by oligomerizing a monomer and having a number average molecular weight in the range of less than 10,000.

In the present invention, 'ethylene oligomerization' means the oligomerization of ethylene. Depending on the number of ethylene polymerized, the 'ethylene oligomerization' is called trimerization or tetramerization, which is collectively referred to as multimerization. An ethylene oligomerization reaction according to an embodiment of the present invention may be to selectively prepare 1-hexene and 1-octene which are main co-monomers of a linear low-density polyethylene.

In the present invention, an 'ethylene oligomerization reaction product' may be a multi-component hydrocarbon in multiple phases including an ethylene oligomerization product, a polymer product, and unreacted ethylene. Among the ethylene oligomerization reaction products, an alpha-olefin is an oligomer having 4 to 40 carbon atoms, specifically 4 to 10 carbon atoms, and examples thereof may be an ethylene dimer having 4 carbon atoms, an ethylene trimer of 6 carbon atoms, and an ethylene tetramer having 8 carbon atoms. The molecular weight of the alpha-olefin may be 1,500 or less, specifically 1,000 or less, but is not limited thereto.

In the present invention, C in C4, C6, C8, C10, and the like means carbon. For example, C6 represents 6 carbon atoms.

In the present invention, a 'fraction' indicates that a certain material has been divided into several groups. For example, an oligomer fraction means that an oligomer has been divided into several groups.

In the present invention, an 'oligomer fraction' is an ethylene oligomerization reaction product excluding ethylene and 1-butene, and means a mixture supplied as a raw material for a first C6 distillation column 21. The 'oligomer fraction' may be obtained by discharging the ethylene oligomerization reaction product from the bottom of a C2/C4 distillation column (not shown) in which the unreacted ethylene and the 1-butene are simultaneously separated, or from the bottom of a C4 distillation column (not shown) in which only the 1-butene is separated, but the embodiment of the present invention is not limited thereto. Specifically, a C6 or more linear alpha-olefin, for example, a C6 hydrocarbon compound such as 1-hexene, a C8 hydrocarbon compound such as 1-octene, a C10 hydrocarbon compound such as 1-decene, and a solvent for dissolving ethylene and a catalyst may be included.

In the present invention, a 'rich fraction' refers to a fraction including a specific component in the fraction, which is composed of several components or mixtures, in a higher ratio than other components. For example, a C6 hydrocarbon compound rich fraction represents a fraction including a C6 hydrocarbon compound in a higher ratio than other components among components constituting the fraction.

A method for separating ethylene oligomerization reaction products of the present invention includes a step of introducing an oligomer fraction excluding unreacted ethylene and 1-butene among ethylene oligomerization reaction products into a cooling unit 24 to be cooled (Step 1).

Step 1 is a step for performing cooling before introducing an ethylene oligomerization reaction product of relatively high temperature and high pressure into a distillation column.

The temperature of an oligomer fraction discharged from a cooling unit 24 may be 50-200° C. The temperature of the ethylene oligomerization reaction product before cooling is typically above 200° C., and may be, for example, 235° C. The temperature is higher than the temperature of a tray positioned at the bottom of a first C6 distillation column 21 so that a load is applied to a condenser 25 connected to the first C6 distillation column 21, resulting in a lot of energy and costs.

Therefore, in the present invention, the temperature is lowered using the cooling unit 24 before the oligomer fraction is introduced into the first C6 distillation column 21. Through the above the load applied to the condenser 25 connected to the first C6 distillation column 21 was reduced and the operation costs required for heat removal may be reduced. At this time, it is preferable that the temperature of the cooled oligomer fraction is controlled to be similar to the temperature of the tray at which raw material are supplied to the first C6 distillation column 21, and the temperature may be 50-200° C. However, the embodiment of the present invention is not limited thereto, and the temperature may vary according to an environment such as process conditions.

As the cooling unit 24, a heat exchanger, a cooler, or both may be used. For more efficient heat removal, a small amount of utility which may be cooled may be simultaneously used in addition to the heat exchanger and the cooler, and the type and number of the utility are not limited.

In the present invention, at least a portion of the oligomer fraction may be used as a heat source for a reboiler 30 of a solvent distillation column 23 to be described later.

In the present invention, heat provided to a reboiler may generated through heat exchange between a high temperature flow and a low temperature flow.

Using at least a portion of the oligomer fraction as a heat source for the reboiler 30 of the solvent distillation column 23 means that, for example, it is possible to heat at least a portion of a third lower fraction discharged from the bottom of the solvent distillation column 23 by heat exchanging the input flow of the cooling unit 24 and the input flow of the reboiler 30 of the bottom of the solvent distillation column 23.

At this time, the heat exchange is performed through the temperature difference between the two flows. Specifically, the heat exchange uses the point in that the temperature of the input flow of the cooling unit 24 is higher than the temperature of the input flow of the reboiler 30 of the bottom of the solvent distillation column 23.

That is, as shown in the FIGURE, the input flow of the cooling unit 24 may be used as a heat source of the reboiler 30 of the solvent distillation column 23 by A heat exchange, and heat lost by the oligomer fraction at the same time as the temperature of the oligomer fraction is lowered may be supplied to the reboiler 30 of the solvent distillation column 23 and used as a heat source.

Through the above, in the present invention, a hot utility, such as steam, which is typically supplied to a reboiler is not used, or used in a small amount compared to a typical method, so that there is a surprising effect in that energy efficiency is increased and the costs required for a separation process are further saved. In addition, the energy required to cool the oligomer fraction of high temperature, such as the usage of cooling water may also be reduced.

In the present invention, the amount of heat supplied as a heat source for the reboiler 30 may vary depending on the amount of an oligomer fraction introduced into the cooling unit 24, the amount of a third lower fraction discharged from the bottom of the solvent distillation column 23, and the degree of heat exchange between the oligomer fraction and the lower fraction.

The method for separating ethylene oligomerization reaction products of the present invention includes introducing the oligomer fraction discharged from the cooling unit 24 into the first C6 distillation column 21 to discharge a first upper fraction from the top of the column and discharge a first lower fraction from the bottom of the column (Step 2), introducing the first upper fraction discharged from the top of the first C6 distillation column into a second C6 distillation column 22 to discharge a second upper fraction from the top of the column and discharge a second lower fraction from the bottom of the column (Step 3), and introducing the first lower fraction discharged from the bottom of the first C6 distillation column 21 into the solvent distillation column 23 to discharge a third upper fraction from the top of the column and discharge a third lower fraction from the bottom of the column (Step 4).

Step 2 is a step of introducing the cooled oligomer fraction into the first C6 distillation column 21 to separate the oligomer fraction into a first upper fraction and a first lower fraction. At this time, the first upper fraction may have a high content ratio of C6 hydrocarbon compound in the fraction, and the first lower fraction may have a low content ratio of C6 hydrocarbon compound in the fraction. That is, the first upper fraction may be a C6 hydrocarbon compound rich fraction, and the components in the fraction may be mostly C6 hydrocarbon compounds, and the first lower fraction may be a C6 hydrocarbon compound deficient fraction including hydrocarbon compounds of C8 or more and a solvent in the fraction.

Step 3 is a step of introducing the recovered first upper fraction into the second C6 distillation column 22 to separate the recovered first upper fraction into a second upper fraction and a second lower fraction. At this time, the second upper fraction may have a high content ratio of 1-hexene in the fraction, and the second lower fraction may have a low content ratio of 1-hexene in the fraction. That is, the second upper fraction may be a 1-hexene rich fraction, and the components in the fraction may be mostly 1-hexene, and the second lower fraction may be a 1-hexene deficient fraction including C6 hydrocarbon compounds excluding 1-hexene in the fraction.

Step 4 is a step of introducing the recovered first lower fraction into the solvent distillation column 23 to separate the recovered first lower fraction into a third upper fraction and a third lower fraction. At this time, the third upper fraction may have a high content ratio of solvent in the fraction, and the third lower fraction may have a low content ratio of solvent in the fraction. That is, the third upper fraction may be a solvent rich fraction, and the components in the fraction may be mostly solvents, and the third lower fraction may be a solvent deficient fraction including hydrocarbon compounds of C8 or more in the fraction.

In the present invention, at least a portion of the third upper fraction may be used as a heat source for the reboiler 26 of the first C6 distillation column 21 and as a heat source for the reboiler 28 of the second C6 distillation column 22.

Using at least a portion of the third upper fraction as a heat source for the reboiler 26 of the first C6 distillation column 21 means that, for example, it is possible to heat at least a portion of the first lower fraction discharged from the bottom of the first C6 distillation column 21 by heat exchanging the input flow of a condenser 29 of the top of the solvent distillation column 23 and the input flow of the reboiler 26 of the bottom of the first C6 distillation column 21.

Using at least a portion of the third upper fraction as a heat source for the reboiler 28 of the second C6 distillation column 22 means that, for example, it is possible to heat at least a portion of the second lower fraction discharged from the bottom of the second C6 distillation column 22 by heat exchanging the input flow of the condenser 29 of the top of the solvent distillation column 23 and the input flow of the reboiler 26 of the bottom of the second C6 distillation column 22.

The heat exchange is performed through the temperature difference between the two flows. Specifically, the heat exchange uses the point in that the temperature of the input flow of the condenser 29 of the top of the solvent distillation column 23 is higher than the temperature of the input flow of the reboiler 26 of the bottom of the first C6 distillation column 21, and the temperature of the input flow of the condenser 29 of the top of the solvent distillation column 23 is higher than the temperature of the input flow of the reboiler 28 of the bottom of the second C6 distillation column 22.

That is, as shown in the FIGURE, the input flow of the condenser 29 of the top of the solvent distillation column 23 may be used as a heat source of the reboiler 26 of the first C6 distillation column 21 by B heat exchange, and may be used as a heat source of the reboiler 28 of the second C6 distillation column 22 by C heat exchange, or as a heat source of two reboilers 26 and 29 by two heat exchanges B and C. Heat lost by the third upper fraction at the same time as the temperature of the third upper fraction discharged from the top of the solvent distillation column 23 is lowered may be supplied to the reboiler 26 of the first C6 distillation column 21 and to the reboiler 28 of the second C6 distillation column 22 and used as a heat source.

Through the above, in the present invention, a hot utility, such as steam, which is typically supplied to a reboiler is not used, or used in a small amount compared to a typical method, so that there is a surprising effect in that energy efficiency is increased and the costs required for a separation process are further saved. In addition, the energy required to condense the discharge flow of the top of the solvent distillation column 23, such as the usage of cooling water may also be reduced.

In the present invention, the amount of heat supplied as a heat source to the reboilers 26 and 28 may vary depending on the amount of the third upper fraction discharged from the top of the solvent distillation column 23, the amount of the first lower fraction discharged from the bottom of the first C6 distillation column 21, the amount of the second lower fraction discharged from the bottom of the second C6 distillation column 22, the degree of heat exchange between the third upper fraction and the first lower fraction, and the degree of heat exchange between the third upper fraction and the second lower fraction.

In the present invention, the heat exchange between the input flow of the condenser 29 of the top of the solvent distillation column 23 and the input flow of the reboiler 26 of the bottom of the first C6 distillation column 21 and the heat exchange between the input of the condenser 29 of the top of the solvent distillation column 23 and the input flow of the reboiler 28 of the bottom of the second C6 distillation column 22 may be more smoothly performed by controlling the operation pressure of the first C6 distillation column 21 and the operation pressure of the solvent distillation column 23.

Specifically, the operation pressure of the first C6 distillation column 21 may be lower than the operation pressure of the solvent distillation column 23. More specifically, the operation pressure of the first C6 distillation column 21 may be −0.5-0 kg/cm$^2$g and the operation pressure of the solvent distillation column 23 may be 0-2 kg/cm$^2$g. The kg/cm$^2$g is a unit for displaying a gauze pressure, and is displayed as 0 kg/cm$^2$g at atmospheric pressure, that is under normal pressure.

The operation pressure of the first C6 distillation column 21 may be equal to or less than normal pressure, and more specifically, may be −0.5-0 kg/cm$^2$g. Particularly, the operation pressure of the first C6 distillation column 21 may be set such that the temperature of the discharge flow of the bottom of the first C6 distillation column 21 is lower than the temperature of the discharge flow of the top of the solvent distillation column 23 by 3° C., preferably 5° C., and more preferably 10° C.

By controlling the operation pressure of the first C6 distillation column 21, the temperature of the discharge flow of the top of the first C6 distillation column 21 may be 120° C. or lower, preferably 110° C. or lower.

As described above, by reducing the operation pressure of the first C6 distillation column 21 to set the temperature of the operation temperature and the temperature of the discharge flow to be low, and the input flow of the reboiler 30 of the bottom of the solvent distillation column 23 is heated by using the input flow of the cooling unit 24 which is relatively high in temperature.

In addition, the operation pressure of the solvent distillation column 23 may be equal to or higher than normal pressure, and may specifically be 0-2 kg/cm$^2$g. As described above, by controlling the operation pressure of the solvent distillation column 23 to be high to increase the temperature of the discharge flow of the top of the solvent distillation column 23 to be higher than the temperature of the discharge flow of another distillation column, for example, the temperature of the discharge flow of each of the bottom of the first C6 distillation column 21 and the bottom of the second C6 distillation column 22, the input flow of the reboiler 26 of the bottom of the first C6 distillation column 21 and the input flow of the reboiler 28 of the bottom of the second C6 distillation column 22 is heated by using the input flow of the top of the solvent distillation column 23.

In the present invention, at least a portion of the oligomer fraction is used as a heat source for the reboiler of the solvent distillation column 23, and at least a portion of the third upper fraction is used as a heat source of the reboilers 26 and 28 of the first C6 distillation column 21 and the second C6 distillation column 22, respectively.

In this case, when compared with a case in which at least a portion of the oligomer fraction is used as a heat source for the reboiler 30 of the solvent distillation column 23, at least a portion of the third upper fraction is used as a heat source for the reboiler 26 of the first C6 distillation column 21, or at least a portion of the third upper fraction is used as a heat source for the reboiler 28 of the second C6 distillation column 22, by using the three heat sources simultaneously in one process, the use of an external hot utility may be significantly reduced.

In the present invention, in order to efficiently operate the reboiler 26 of the first C6 distillation column 21, the reboiler 28 of the second C6 distillation column 22, and the reboiler 30 of the solvent distillation column 23 in terms of energy, the calories supplied from the reboiler 26 connected to the bottom or side of the first C6 distillation column 21 should be similar to the calories to be removed from the condenser 25 connected to the top of the first C6 distillation column 21, the calories supplied from the reboiler 28 connected to the bottom or side of the second C6 distillation column 22 should be similar to the calories to be removed from the condenser 27 connected to the top of the second C6 distillation column 22, and the calories supplied from the reboiler 30 connected to the bottom or side of the solvent distillation column 23 should be similar to the calories to be removed from the condenser 29 connected to the top of the solvent distillation column 23. When the calories supplied to the reboilers 26, 28, and 30 according to the separation method of the present invention are not sufficient, it is possible to enable an additional heat supply using a hot utility including steam that has been typically used as a heat source for a reboiler.

The method for separating ethylene oligomerization reaction products according to the present invention is applicable to most processes of separating ethylene oligomerization reaction products, so that the method may be used in a process of separating various types of ethylene oligomerization reaction products.

In the present invention, an ethylene oligomerization may be initiated by using a chromium (Cr)-based or titanium (Ti)-based catalyst such that an oligomer such as 1-hexene and 1-octene are to be selectively produced.

The method for separating ethylene oligomerization reaction products according to the present invention may further include a step of sequentially transferring reaction products to a distillation column of alpha-olefin of C8 or more. The oligomer fraction of the present invention may include a hydrocarbon compound of C8 or more according to polymerization conditions. Accordingly, if necessary, the step of sequentially transferring the reaction products passing through the solvent distillation column 23 to the distillation column of alpha-olefin of C8 or more may be further included.

EXAMPLES

Hereinafter, the present invention will be described in detail with reference to Examples. However, the following Examples are merely illustrative of the present invention and are not intended to limit the scope of the present invention.

In the following Examples and Comparative Examples, the separation method according to the present invention was simulated using Aspen Plus, which is a commercial process simulation program. As constants required for the simulation, values embedded on the program, values described in the literature, and the like were used.

A mixed solution for an ethylene oligomerization reaction was set to include an ethylene monomer, a chromium-based catalyst, and methylcyclohexane as a solvent.

Example 1: Separation of Ethylene Oligomerization Reaction Products

First, using a process shown in the FIGURE, separation of ethylene oligomerization reaction products was performed.

Specifically, a polymerization reaction is performed with a mixed solution containing an ethylene monomer, a chromium-based catalyst and methylcyclohexane, and then among reaction products, unreacted ethylene and 1-butene were separated using a C2/C4 distillation column (not shown) or a C4 distillation column (not shown). The remaining reaction products were transferred to the next step. Thereafter, in order to lower the temperature before supplying an oligomer fraction to the first C6 distillation column 21, cooling was performed using the cooling unit 24.

The cooled oligomer fraction was introduced into the first C6 distillation column 21 to be separated into a first upper fraction and a first lower fraction. The first upper fraction was introduced into the second C6 distillation column 22 as a first upper fraction recovery flow 13 through the condenser 25. In the second C6 distillation column 22, separation into a second upper fraction and a second lower fraction was performed, and the second upper fraction was recovered as a second upper fraction recovery flow 14 through the condenser 27, and the second lower fraction was recovered as a second lower fraction recovery flow 15 through the reboiler 28. Meanwhile, the first lower fraction was introduced into the solvent distillation column 23 through the reboiler 26. In the solvent distillation column 23, separation into a third upper fraction and a third lower fraction was performed, and the third upper fraction was recovered as a third upper fraction recovery flow 17 through the condenser 29, and the third lower fraction was recovered as a third lower fraction recovery flow 18 through the reboiler 30.

Table 1 below shows the set values of the pressure and temperature in each flow and the composition of a separated material.

TABLE 1

|  |  | Flow | | | | | | | |
| --- | --- | --- | --- | --- | --- | --- | --- | --- | --- |
|  |  | 1 | 2 | 3 | 4 | 5 | 6 | 7 | 8 |
| Pressure [kg/cm$^2$g] | | 18 | 18 | −0.5 | 0 | 0.5 | 0 | 0.5 | 1 |
| Temperature [° C.] | | 235 | 167 | 40 | 64 | 91 | 107 | 117 | 156 |
| Composition (Mass fraction) | 1-hexene | 0.14 | 0.14 | 0.93 | 0.99 | 0 | 0 | 0 | 0 |
| | C6 hydrocarbons except 1-hexene | 0.18 | 0.18 | 0.07 | 0.01 | 1 | 0.02 | 0.04 | 0 |
| | 1-octene | 0.51 | 0.51 | 0 | 0 | 0 | 0.60 | 0.96 | 0 |
| | C8 or higher hydrocarbons | 0.17 | 0.17 | 0 | 0 | 0 | 0.38 | 0 | 1 |

11: Cooling unit input flow
12: Cooling unit discharge flow
13: First upper fraction recovery flow
14: Second upper fraction recovery flow
15: Second lower fraction recovery flow
16: First lower fraction recovery flow
17: Third upper fraction recovery flow
18: Third lower fraction recovery flow In Example 1, a portion of the oligomer fraction of the input flow of the cooling unit 24 was used as a heat source for the reboiler 30 of the solvent distillation column 23, and a portion of the third upper fraction was used as a heat source for the reboilers 26 and 28 of the first C6 distillation column 21 and the second C6 distillation column 22, respectively.

As shown in Table 1 above, the pressure of each of the discharge flows 13, 14, and 17 of the top of each of the first C6 distillation column 21, the second C6 distillation column 22, and the solvent distillation column 23 were −0.5 kg/cm$^2$g, 0 kg/cm$^2$g, and 0.5 kg/cm$^2$g, respectively.

As shown in Table 1 above, it was confirmed that the first upper fraction recovery flow 13 of the top of the first C6 distillation column 21 and the first lower fraction recovery flow 16 of the bottom thereof were both low in temperature and pressure by operating the first C6 distillation column 21 at a low pressure. In addition, it was confirmed that, as the solvent distillation column 23 was operated at a high pressure, the third upper fraction recovery flow 17 of the top of the solvent distillation column 23 and the third lower fraction recovery flow 18 of the bottom thereof were both high in temperature and pressure.

Using the above, a portion of the oligomer fraction of the input flow of the cooling unit 24 was used as a heat source for the reboiler 30 of the solvent distillation column 23, and since the temperature of the third upper fraction recovery flow 17 was higher than the temperature of the first lower fraction recovery flow 16, a portion of the third upper fraction was used as a heat source for the reboilers 26 and 28 of the first C6 distillation column 21 and the second distillation column 22, respectively.

Comparative Example 1: Separation of Ethylene Oligomerization Reaction Products

A portion of the oligomer fraction of the input flow of the cooling unit 24 was used as a heat source for the reboiler 26 of the first C6 distillation column 21, and steam was used as a heat source for the rest of the reboilers. Ethylene oligomerization reaction products were separated in the same manner as in Example 1 except for the above.

Table 2 below shows the set values of the pressure and temperature in each flow and the composition of a separated material.

TABLE 2

| | | Flow | | | | | | | |
|---|---|---|---|---|---|---|---|---|---|
| | | 11 | 12 | 13 | 14 | 15 | 16 | 17 | 18 |
| Pressure [kg/cm$^2$g] | | 18 | 18 | 0 | 0 | 0.5 | 0.5 | 0 | 0.5 |
| Temperature [° C.] | | 235 | 189 | 64 | 64 | 91 | 124 | 101 | 143 |
| Composition (Mass fraction) | 1-hexene | 0.14 | 0.14 | 0.93 | 0.99 | 0 | 0 | 0 | 0 |
| | C6 hydrocarbons except 1-hexene | 0.18 | 0.18 | 0.07 | 0.01 | 1 | 0.02 | 0.04 | 0 |
| | 1-octene | 0.51 | 0.51 | 0 | 0 | 0 | 0.60 | 0.96 | 0 |
| | C8 or higher hydrocarbons | 0.17 | 0.17 | 0 | 0 | 0 | 0.38 | 0 | 1 |

Comparative Example 2: Separation of Ethylene Oligomerization Reaction Products

By operating the first C6 distillation column 21 at normal pressure (0 kg/cm$^2$g), a portion of the oligomer fraction of the input flow of the cooling unit 24 was used as a heat source for the reboiler 30 of the solvent distillation column 23, steam was used as a heat source for the rest of the reboilers. Ethylene oligomerization reaction products were separated in the same manner as in Example 1 except for the above.

Table 3 below shows the set values of the pressure and temperature in each flow and the composition of a separated material.

TABLE 3

| | | Flow | | | | | | | |
|---|---|---|---|---|---|---|---|---|---|
| | | 11 | 12 | 13 | 14 | 15 | 16 | 17 | 18 |
| Pressure [kg/cm$^2$g] | | 18 | 18 | 0 | 0 | 0.5 | 0.5 | 0 | 0.5 |
| Temperature [° C.] | | 235 | 153 | 64 | 64 | 91 | 124 | 101 | 143 |
| Composition (Mass fraction) | 1-hexene | 0.14 | 0.14 | 0.93 | 0.99 | 0 | 0 | 0 | 0 |
| | C6 hydrocarbons except 1-hexene | 0.18 | 0.18 | 0.07 | 0.01 | 1 | 0.02 | 0.04 | 0 |
| | 1-octene | 0.51 | 0.51 | 0 | 0 | 0 | 0.60 | 0.96 | 0 |
| | C8 or higher hydrocarbons | 0.17 | 0.17 | 0 | 0 | 0 | 0.38 | 0 | 1 |

Comparative Example 3: Separation of Ethylene Oligomerization Reaction Products

By operating the first C6 distillation column 21 at less than normal pressure (−0.5 kg/cm$^2$g), a portion of the third upper fraction was used as a heat source for the reboiler 26 of the first C6 distillation column 21, and steam was used as a heat source for the rest of the reboilers. Ethylene oligomerization reaction products were separated in the same manner as in Example 1 except for the above.

Table 4 below shows the set values of the pressure and temperature in each flow and the composition of a separated material.

TABLE 4

| | | Flow | | | | | | | |
|---|---|---|---|---|---|---|---|---|---|
| | | 11 | 12 | 13 | 14 | 15 | 16 | 17 | 18 |
| Pressure [kg/cm$^2$g] | | 18 | 18 | −0.5 | 0 | 0.5 | 0 | 0.5 | 1.0 |
| Temperature [° C.] | | 235 | 235 | 40 | 64 | 91 | 107 | 117 | 156 |
| Composition (Mass fraction) | 1-hexene | 0.14 | 0.14 | 0.93 | 0.99 | 0 | 0 | 0 | 0 |
| | C6 hydrocarbons except 1-hexene | 0.18 | 0.18 | 0.07 | 0.01 | 1 | 0.02 | 0.04 | 0 |
| | 1-octene | 0.51 | 0.51 | 0 | 0 | 0 | 0.60 | 0.96 | 0 |
| | C8 or higher hydrocarbons | 0.17 | 0.17 | 0 | 0 | 0 | 0.38 | 0 | 1 |

Comparative Example 4: Separation of Ethylene Oligomerization Reaction Products

By operating the first C6 distillation column 21 at normal pressure (0 kg/cm$^2$g), a portion of the third upper fraction was used as a hear source for the reboiler 28 of the second C6 distillation column 22, and steam was used as a heat source for the rest of the reboilers. Ethylene oligomerization reaction products were separated in the same manner as in Example 1 except for the above.

Table 5 below shows the set values of the pressure and temperature in each flow and the composition of a separated material.

TABLE 5

| | | Flow | | | | | | | |
|---|---|---|---|---|---|---|---|---|---|
| | | 11 | 12 | 13 | 14 | 15 | 16 | 17 | 18 |
| Pressure [kg/cm$^2$g] | | 18 | 18 | 0 | 0 | 0.5 | 0.5 | 0 | 0.5 |
| Temperature [° C.] | | 235 | 153 | 64 | 64 | 91 | 124 | 101 | 143 |
| Composition (Mass fraction) | 1-hexene | 0.14 | 0.14 | 0.93 | 0.99 | 0 | 0 | 0 | 0 |
| | C6 hydrocarbons except 1-hexene | 0.18 | 0.18 | 0.07 | 0.01 | 1 | 0.02 | 0.04 | 0 |
| | 1-octene | 0.51 | 0.51 | 0 | 0 | 0 | 0.60 | 0.96 | 0 |
| | C8 or higher hydrocarbons | 0.17 | 0.17 | 0 | 0 | 0 | 0.38 | 0 | 1 |

Comparative Example 5: Separation of Ethylene Oligomerization Reaction Products

By operating the first C6 distillation column 21, the second C6 distillation column 22, and the solvent distillation column 23 at normal pressure (0 kg/cm$^2$g), heat generated inside was not used as a heat source, but only steam, which is external hot utility, was used as a heat source. Ethylene oligomerization reaction products were separated in the same manner as in Example 1 except for the above.

Table 6 below shows the set values of the pressure and temperature in each flow and the composition of a separated material.

TABLE 6

|  |  | Flow | | | | | | | |
|---|---|---|---|---|---|---|---|---|---|
|  |  | 11 | 12 | 13 | 14 | 15 | 16 | 17 | 18 |
| Pressure [kg/cm²g] | | 18 | 18 | 0 | 0 | 0.5 | 0.5 | 0 | 0.5 |
| Temperature [° C.] | | 235 | 235 | 65 | 64 | 91 | 124 | 101 | 143 |
| Composition (Mass fraction) | 1-hexene | 0.14 | 0.14 | 0.93 | 0.99 | 0 | 0 | 0 | 0 |
| | C6 hydrocarbons except 1-hexene | 0.18 | 0.18 | 0.07 | 0.01 | 1 | 0.02 | 0.04 | 0 |
| | 1-octene | 0.51 | 0.51 | 0 | 0 | 0 | 0.60 | 0.96 | 0 |
| | C8 or higher hydrocarbons | 0.17 | 0.17 | 0 | 0 | 0 | 0.38 | 0 | 1 |

Experimental Example 1: Evaluation of Energy Efficiency in Ethylene Oligomerization Reaction Product Separation Process After performing the separation process of the ethylene oligomerization reaction products according to each of Example 1 and Comparative Examples 1 to 5, the energy usage in each process was measured and the results are shown in Tables 7 to 9 below.

TABLE 7

|  | Example 1 | | | Comparative Example 1 | | |
|---|---|---|---|---|---|---|
| Steam usage [Gcal/hr] | 2.35 | | | 3.31 | | |
| Reboiler | First C6 distillation column reboiler | Second C6 distillation column reboiler | Solvent distillation column Reboiler | First C6 distillation column reboiler | Second C6 distillation column reboiler | Solvent distillation column reboiler |
| Energy usage [Gcal/hr] | 0.53 | 1.11 | 3.13 / 0.78  2.35 | 0.55 | 1.09 | 2.22 |
| Energy source | Third upper fraction | Third upper fraction | Oligomer fraction  Steam | Oligomer fraction | Steam | Steam |

TABLE 8

|  | Comparative Example 2 | | | Comparative Example 3 | | |
|---|---|---|---|---|---|---|
| Steam usage [Gcal/hr] | 3.01 | | | 4.24 | | |
| Reboiler | First C6 distillation column reboiler | Second C6 distillation column reboiler | Solvent distillation column Reboiler | First C6 distillation column reboiler | Second C6 distillation column reboiler | Solvent distillation column reboiler |
| Energy usage [Gcal/hr] | 0.63 | 1.09 | 2.22 / 0.93  1.29 | 0.43 | 1.11 | 3.13 |
| Energy source | Steam | Steam | Oligomer fraction  Steam | Third upper fraction | Steam | Steam |

TABLE 9

|  | Comparative Example 4 | | | Comparative Example 5 | | |
|---|---|---|---|---|---|---|
| Steam usage [Gcal/hr] | 3.14 | | | 3.79 | | |
| Reboiler | First C6 distillation column reboiler | Second C6 distillation column reboiler | Solvent distillation column Reboiler | First C6 distillation column reboiler | Second C6 distillation column reboiler | Solvent distillation column reboiler |

TABLE 9-continued

|  | Comparative Example 4 | | | Comparative Example 5 | | |
| --- | --- | --- | --- | --- | --- | --- |
| Energy usage [Gcal/hr] | 0.92 | 1.09 | 2.22 | 0.48 | 1.09 | 2.22 |
| Energy source | Steam | Third upper fraction | Steam | Steam | Steam | Steam |

In summary, Comparative Example 1 is one in which a portion of the oligomer fraction was used as a heat source for the reboiler 26 of the first C6 distillation column 21, and Comparative Example 2 is one in which only A heat exchange was used. Comparative Example 3 is one which only B heat exchange was used, and Comparative Example 4 is one in which C heat exchange was used. Comparative Example 5 is one in which an external hot utility was used without internal heat exchange. As it can be seen from Tables 7 to 9, in the case of Example 1 in which a portion of the oligomer fraction was used as a heat source for the reboiler 30 of the solvent distillation column 23 and a portion of the third upper fraction was used as a heat source for the reboilers 26 and 28 of the first C6 distillation column 21 and the second C6 distillation column 22, respectively to use all of the A to C heat exchanges, the usage of steam, which is an external hot utility, was only 2.5 Gcal/hr. When comparing with Comparative Example 5 in which only steam was used as a heat source without heat exchange, the usage of steam was reduced from 3.79 Gcal/hr to 2.35 Gcal/hr, which is a very surprising energy efficiency achievement.

In addition, in the case of Comparative Example 1 in which a portion of the oligomer fraction was used as a heat source for the reboiler 26 of the first C6 distillation column 21, the usage of steam was slightly reduced when compared with that of Comparative Example 5, but a lot of steam was still required.

As in Comparative Examples 2 to 4 in which only one among A heat exchange, B heat exchange, and C heat exchange was performed, a lot more steam was used when compared with Example 1. Specifically, in Comparative Examples 2 to 4, the usage of steam all exceeded 3 Gcal/hr, and in the case of Comparative Example 2, the usage of steam was about 130% higher than that of Example 1 (3.01 Gcal/hr compared with 2.35 Gcal/hr), in the case of Comparative Example 3, the usage was about 180% higher (4.24 Gcal/hr compared with 2.35 Gcal/hr), and in the case of Comparative Example 4, the usage was about 134% higher (3.14 Gcal/hr compared with 2.35 Gcal/hr).

On the contrary, in the case of Example 1 in which all of the A, B, C heat exchanges were performed to utilize an internal heat source, the usage of steam was greatly reduced to 2.35 Gcal/hr, resulting in greatly improving the efficiency and economic feasibility of the separation process.

Accordingly, even when the amount of energy used in a reboiler was equal or similar, the most of the energy used in the reboiler of Example 1 was one utilizing heat generated internally, the energy efficiency was greatly increased when compared to that of Comparative Example 1 and Comparative Example 2. In addition, while the energy efficiency was increased as described above, there was no change in the composition ratio of materials contained in each flow. Through the above, it was confirmed that even an internal heat source is used, the distillation column was smoothly operated without affecting the performance of the process of separating ethylene oligomerization reaction products.

DESCRIPTION OF SYMBOLS

11: Cooling unit input flow
12: Cooling unit discharge flow
13: First upper fraction recovery flow
14: Second upper fraction recovery flow
15: Second lower fraction recovery flow
16: First lower fraction recovery flow
17: Third upper fraction recovery flow
18: Third lower fraction recovery flow
21: First C6 distillation column
22: Second C6 distillation column
23: Solvent distillation column
24: Cooling unit
25: First C6 distillation column condenser
26: First C6 distillation column reboiler
27: Second C6 distillation column condenser
28: Second C6 distillation column reboiler
29: Solvent distillation column condenser
30: Solvent distillation column reboiler

The invention claimed is:
1. A method for separating ethylene oligomerization reaction products, comprising:
   introducing an oligomer fraction excluding unreacted ethylene and 1-butene among ethylene oligomerization reaction products into a cooling unit to be cooled;
   introducing the oligomer fraction discharged from the cooling unit into a first C6 distillation column to discharge a first upper fraction from a top of the first C6 distillation column and discharge a first lower fraction from a bottom of the first C6 distillation column;
   introducing the first upper fraction discharged from the top of the first C6 distillation column into a second C6 distillation column to discharge a second upper fraction from a top of the second C6 distillation column and discharge a second lower fraction from a bottom of the second C6 distillation column; and
   introducing the first lower fraction discharged from the bottom of the first C6 distillation column into a solvent distillation column to discharge a third upper fraction from a top of the solvent distillation column and discharge a third lower fraction from a bottom of the solvent distillation column,
   wherein the first C6 distillation column, the second C6 distillation column, and the solvent distillation column are each provided with a condenser and a reboiler,
   at least a portion of the oligomer fraction is used as a reboiler heat source for the solvent distillation column, and
   at least a portion of the third upper fraction is used as a reboiler heat source for each of the first C6 distillation column and the second C6 distillation column.

2. The method of claim 1, wherein an operation pressure of the first C6 distillation column is −0.5- to 0 kg/cm²g, and an operation pressure of the solvent distillation column is 0- to 2 kg/cm²g.

3. The method of claim 1, wherein a temperature of the oligomer fraction discharged from the cooling unit is 50- to 200° C.

4. The method of claim 1, wherein the cooling unit comprises a heat exchanger and a cooler.

5. The method of claim 1, wherein heat provided to the reboiler of the solvent distillation column is generated through heat exchange between the input flow of the cooling unit and the input flow of the reboiler of the bottom of the solvent distillation column.

6. The method of claim 1, wherein heat provided to the reboiler of the first C6 distillation column is generated through heat exchange between the input flow of the condenser of the top of the solvent distillation column and the input flow of the reboiler of the bottom of the first C6 distillation column.

7. The method of claim 1, wherein heat provided to the reboiler of the second C6 distillation column is generated through heat exchange between the input flow of the condenser of the top of the solvent distillation column and the input flow of the reboiler of the bottom of the second C6 distillation column.

8. The method of claim 1, wherein the oligomer fraction comprises a C6 or more linearalpha olefin and a solvent used for dissolving ethylene and a catalyst during the oligomerization reaction.

9. The method of claim 8, wherein the C6 or more linear alpha olefin comprises 1-hexene, 1-octene, and 1-decene.

10. The method of claim 1, wherein an alpha olefin produced by the ethylene oligomerization is a C4 to C40 oligomer.

11. The method of claim 10, wherein the molecular weight of the alpha olefin is 1,500 or less.

* * * * *